(12) United States Patent
Mohara et al.

(10) Patent No.: US 10,408,166 B2
(45) Date of Patent: Sep. 10, 2019

(54) GAS ANALYSIS DEVICE, GAS SAMPLING DEVICE AND GAS ANALYSIS METHOD

(71) Applicant: HORIBA, Ltd., Kyoto (JP)

(72) Inventors: Haruhisa Mohara, Kyoto (JP);
Takeshi Kusaka, Kyoto (JP)

(73) Assignee: HORIBA, LTD., Kyoto (JP)

( * ) Notice: Subject to any disclaimer, the term of this patent is extended or adjusted under 35 U.S.C. 154(b) by 174 days.

(21) Appl. No.: 15/672,558

(22) Filed: Aug. 9, 2017

(65) Prior Publication Data

US 2018/0163666 A1 Jun. 14, 2018

(30) Foreign Application Priority Data

Dec. 14, 2016 (JP) ................................. 2016-242686
Mar. 31, 2017 (JP) ................................. 2017-070648

(51) Int. Cl.
*G01M 15/10* (2006.01)
*F02M 21/02* (2006.01)
(Continued)

(52) U.S. Cl.
CPC .......... *F02M 21/0209* (2013.01); *B01J 20/02* (2013.01); *B60K 15/07* (2013.01);
(Continued)

(58) Field of Classification Search
CPC ......... B01J 20/02; B60K 15/07; G01M 15/00; G01M 15/10; G01N 1/2252;
(Continued)

(56) References Cited

U.S. PATENT DOCUMENTS 4,379,402 A * 4/1983 Harman, III ....... G01N 33/0016
422/52
5,073,753 A 12/1991 Collings et al.
(Continued)

FOREIGN PATENT DOCUMENTS

| EP | 0851222 A1 | 7/1998 |
| JP | 60-020146 A | 2/1985 |
| JP | 08-035950 A | 2/1996 |

OTHER PUBLICATIONS

EESR dated Jan. 3, 2018 issued for European Patent Application No. 17 184 565.4.

*Primary Examiner* — Nguyen Q. Ha
(74) *Attorney, Agent, or Firm* — Brooks Kushman P.C.

(57) ABSTRACT

A gas analysis device is provided that is able to accurately measure a concentration or a quantity of methane contained in a sample gas even if there are variations in the pressure in the sample gas line. This gas analysis device has a sample gas line through which a sample gas flows, a pressure loss mechanism that is provided on the sample gas line, a pressure control mechanism that refers to the pressure on the forward side of the pressure loss mechanism and, by discharging a portion of the sample gas from the rearward side of the pressure loss mechanism, and by supplying a predetermined gas to the rearward side of the pressure loss mechanism, controls pressure differences in the sample gas line between the front and the rear of the pressure loss mechanism, and an analyzer that analyzes the sample gas flowing through the sample gas line.

16 Claims, 6 Drawing Sheets

(51) Int. Cl.
*F17C 11/00* (2006.01)
*B60K 15/07* (2006.01)
*G01N 29/028* (2006.01)
*B01J 20/02* (2006.01)
*G01N 1/22* (2006.01)
*G01N 33/00* (2006.01)

(52) U.S. Cl.
CPC .......... *F17C 11/007* (2013.01); *G01N 1/2252* (2013.01); *G01N 29/028* (2013.01); *G01N 33/0016* (2013.01); *G01N 33/0047* (2013.01); *Y02E 60/321* (2013.01); *Y02T 10/32* (2013.01)

(58) Field of Classification Search
CPC .. G01N 29/028; G01N 33/00; G01N 33/0016; G01N 33/0047; F02M 21/02; F17C 11/007; Y02E 60/321; Y02T 10/32
See application file for complete search history.

(56) References Cited

U.S. PATENT DOCUMENTS

| | | | | |
|---|---|---|---|---|
| 5,221,517 | A * | 6/1993 | Takeda | G01N 33/0014 422/54 |
| 5,852,227 | A | 12/1998 | Garthe | |
| 6,505,524 | B1 * | 1/2003 | Silvis | G01N 1/2252 73/863.03 |
| 6,623,699 | B1 * | 9/2003 | Pack | G01N 31/12 422/78 |
| 2003/0136176 | A1 * | 7/2003 | Ruiz | G01N 33/0016 73/23.2 |
| 2013/0014560 | A1 * | 1/2013 | Wei | G01N 1/2252 73/23.31 |
| 2014/0251031 | A1 * | 9/2014 | Kumagai | G01N 1/2252 73/863.41 |

* cited by examiner

GAS ANALYSIS DEVICE, GAS SAMPLING DEVICE AND GAS ANALYSIS METHOD

CROSS-REFERENCE TO RELATED APPLICATIONS

This application claims priority to JP Application Nos. 2016-242686, filed Dec. 14, 2016, and 2017-070648, filed Mar. 31, 2017, the disclosures of which are incorporated in their entirety by reference herein.

TECHNICAL FIELD

The present invention relates to a gas analysis device that analyzes components of a sample gas such as, for example, automobile exhaust gas and the like, and to a gas sampling device that captures a sample gas.

TECHNICAL BACKGROUND

As is shown, for example, in Patent document 1, one method of measuring methane contained in a sample gas such as exhaust gas or the like is to cause the sample gas to pass through a non-methane cutter so that hydrocarbons excluding methane that are contained in the sample gas are combusted inside the non-methane cutter.

During this combustion, in order to prevent the methane from over-combusting due to excessive oxygen, or to prevent the hydrocarbons other than methane from not combusting completely due to insufficient oxygen, it is necessary for the correct ratio of oxygen to be supplied to the sample gas.

However, in this type of gas analysis device, there are cases when, for example, the flow rate of the sample gas varies due to pulsations in the sampling pump, or due to pressure variations in the introduced sample gas or the like.

As a result of this, because there are variations in the mixture ratio between the sample gas and oxygen, the problem arises that there are also variations in the concentration and quantity of the methane being measured.

This type of problem is also evident in gas analysis devices other than those that measure methane.

DOCUMENTS OF THE PRIOR ART

Patent Documents

[Patent document 1] Japanese Unexamined Patent Application (JP-A) No. H08-035950

DISCLOSURE OF THE INVENTION

Problems to be Solved by the Invention

The present invention was conceived in view of the above-described problems, and it is an object thereof to provide a gas analysis device or a gas sampling device that enable a flow rate of a sample gas being captured to be kept constant even when there are variations in the sample gas line.

Means for Solving the Problem

Namely, the gas analysis device according to the present invention is provided with a sample gas line through which a sample gas flows, a pressure loss mechanism that is provided on the sample gas line, a pressure control mechanism that controls pressure differences in the sample gas line between a front and a rear of the pressure loss mechanism by discharging a portion of the sample gas from a rearward side of the pressure loss mechanism, or by supplying a predetermined gas to the rearward side of the pressure loss mechanism, and an analyzer that analyzes the sample gas flowing through the sample gas line.

According to the above-described gas analysis device, even if there are variations in the pressure in the sample gas line, because the flow rate of the sample gas being captured can be kept constant, it is possible to accurately analyze components contained in the sample gas.

Moreover, even in cases in which, for example, the sample gas is mixed with an operating gas or diluent gas or the like, because it is possible to maintain a constant mixture ratio between the sample gas and the operating gas or diluent gas or the like, it is possible to accurately analyze the components contained in the sample gas.

An example of a specific embodiment of the present invention is a structure in which the pressure control mechanism is provided with a sample gas discharge line that discharges a portion of the sample gas in the sample gas line from a rearward side of the pressure loss mechanism, a sample pressure adjustment line that is connected to the sample gas discharge line, and a sample pressure control device that controls pressure differences between the pressure in the sample gas line on the forward side of the pressure loss mechanism and the pressure in the sample pressure adjustment line by referring to the pressure in the sample gas line on the forward side of the pressure loss mechanism.

An example of another embodiment of the present invention is a structure in which the pressure control mechanism is provided with a gas supply line that supplies a predetermined gas to the sample gas line on the rearward side of the pressure loss mechanism on the sample gas line, a pressure control valve that is provided on the gas supply line, and a differential pressure gauge that detects pressure differences between the front and the rear of the pressure loss mechanism, wherein the pressure control valve is controlled based on the pressure differences detected by the differential pressure gauge.

A more specific example of an embodiment of the present invention is a structure in which the sample pressure control device refers to the pressure on the forward side of the pressure loss mechanism, and controls the pressure in the sample pressure adjustment line such that pressure differences between the pressure in the sample gas line on the forward side of the pressure loss mechanism and the pressure in the sample pressure adjustment line remain constant.

More specifically, the pressure loss mechanism may be any one of a capillary tube, an orifice, or a back pressure valve.

If the gas analysis device is further provided with a first gas supply line that supplies a first gas to the sample gas line on the rearward side of the pressure loss mechanism, and with a first gas pressure adjustment mechanism that, by referring to the pressure in the sample gas line on the rearward side of the pressure loss mechanism, maintains a constant difference between a supply side pressure in the first gas supply line and the pressure in the sample gas line, then even if there are variations in the pressure in the sample gas line, because the flow rate of the first gas that is being supplied can be kept constant, the mixture ratio of the sample gas and the first gas can be kept constant.

An example of a specific embodiment of the present invention is a structure in which an oxidation catalyst that removes hydrocarbon components other than methane from the sample gas is further provided on the rearward side of the discharge line.

If the gas analysis device is further provided with a second gas supply line that supplies a second gas to the sample gas line on the rearward side of the pressure loss mechanism, and with a second gas pressure adjustment mechanism that, by referring to the pressure in the sample gas line on the rearward side of the pressure loss mechanism, maintains a constant difference between a supply side pressure in the second gas supply line and the pressure in the sample gas line, then even if there are variations in the pressure in the sample gas line, because the flow rate of the second gas that is being supplied can be kept constant, the mixture ratio of the sample gas and the second gas can be kept constant.

If a structure is employed in which the first gas is oxygen and the second gas is hydrogen, and a water supply catalyst that causes the first gas and the second gas to react so as to create water is further provided in the gas analysis device on the forward side of the oxidation catalyst, then because water can be supplied to the oxidation catalyst, it is possible to prevent excessive combustion of the methane components in the sample gas.

If the quantity of the first gas that is supplied is greater than the quantity of the first gas that reacts with the second gas, then because it is possible to supply the oxygen that is required in the oxidation catalyst to combust non-methane components, any deterioration of the oxidation catalyst can be suppressed.

As is described above, because the quantity of the first gas that is supplied is greater than the quantity of the first gas that reacts with the second gas, the sample gas is diluted in the gas analysis device by the first gas that remains as a result of the reaction between the first gas and the second gas.

If a structure is employed in which the gas analysis device is further provided with a suction type of sampling pump that is disposed downstream from a measurement device on the sample gas line, then because pressure variations in the sample gas line are easily generated by this suction type of sampling pump, the effects provided by the present invention are particularly conspicuous.

An example of a specific embodiment of the gas analysis device is a structure in which the sample gas is exhaust gas emitted from a vehicle, and the gas analysis device is a vehicle-mounted type of gas analysis device.

The effects of the present invention described above can also be achieved in the same way using a gas sampling device that is provided with a sample gas line through which a sample gas flows, a pressure loss mechanism that is provided on the sample gas line, and a pressure control mechanism that controls pressure differences in the sample gas line between a front and a rear of the pressure loss mechanism by discharging a portion of the sample gas from a rearward side of the pressure loss mechanism, or by supplying a predetermined gas to the rearward side of the pressure loss mechanism.

Moreover, a gas analysis method according to the present invention is a gas analysis method that employs a gas analysis device that is provided with a sample gas line through which a sample gas flows, a pressure loss mechanism that is provided on the sample gas line, and an analyzer that analyzes the sample gas flowing through the sample gas line, wherein pressure differences in the sample gas line between a front and a rear of the pressure loss mechanism are controlled by discharging a portion of the sample gas from a rearward side of the pressure loss mechanism, or by supplying a predetermined gas to the rearward side of the pressure loss mechanism. If this type of method is used, then the same effects can be obtained as those obtained from the above-described gas analysis device.

Effects of the Invention

According to the gas analysis device or the gas sampling device according to the present invention, even if there are variations in the pressure in the sample gas line, because the flow rate of the sample gas being captured can be kept constant, it is possible to accurately analyze components contained in the sample gas.

Moreover, even in cases in which, for example, the sample gas is mixed with an operating gas or diluent gas or the like, because it is possible to maintain a constant mixture ratio between the sample gas and the operating gas or diluent gas or the like, it is possible to accurately analyze the components contained in the sample gas.

BEST EMBODIMENTS FOR IMPLEMENTING THE INVENTION

Hereinafter, a first embodiment of a gas analysis device 1 according to the present invention will be described with reference made to the drawings.

A gas analysis device 1 according to the present embodiment analyzes components contained in a sample gas such as, for example, exhaust gas emitted from an internal combustion engine of a vehicle.

Figure 1:
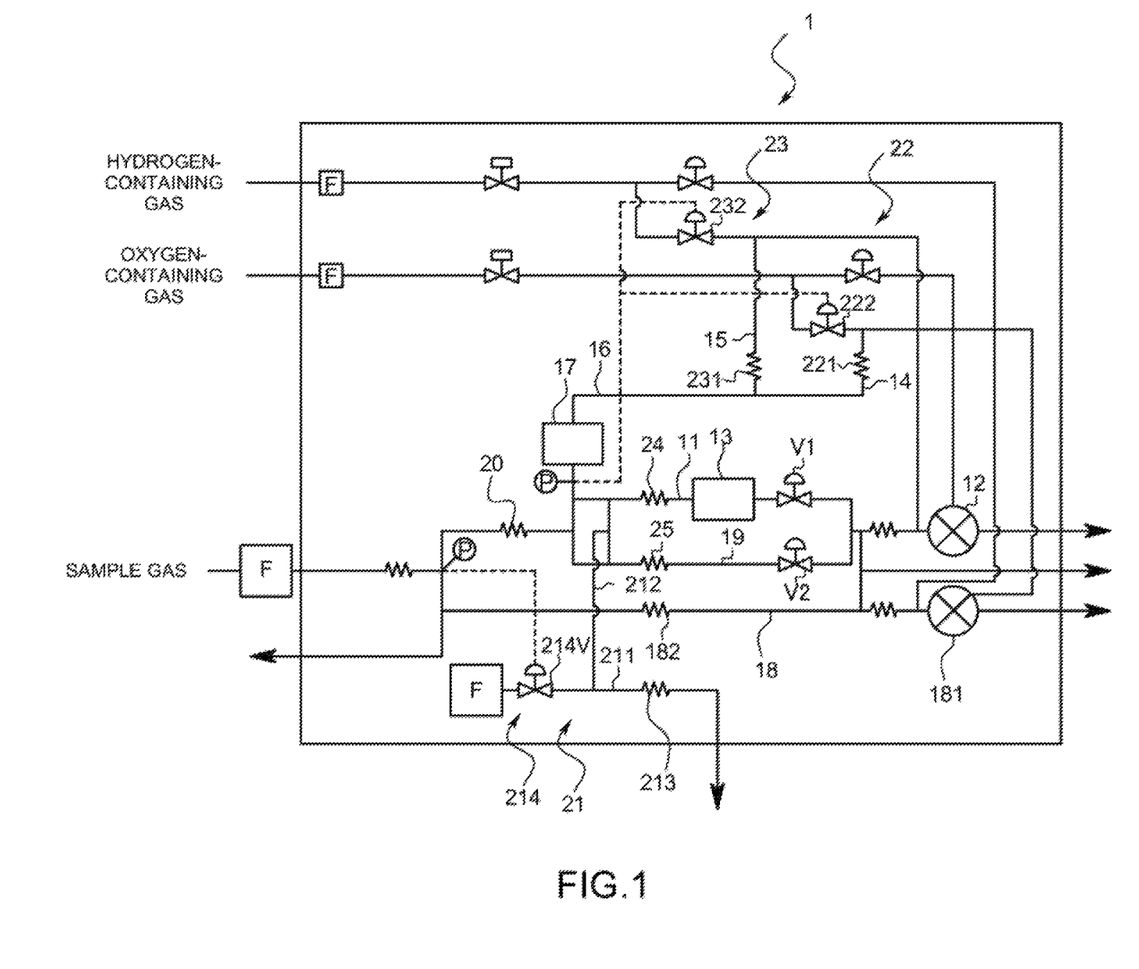
FIG. 1 is a typical view showing the structure of a gas analysis device according to a first embodiment of the present invention.

Specifically, as is shown in FIG. 1, the gas analysis device 1 is provided with a sample gas line 11 through which a sample gas flows, a methane analyzer (i.e., a first analyzer) 12 that is provided on the sample gas line 11 and analyzes methane contained in the sample gas, a non-methane cutter 13 that is provided upstream from the methane analyzer 12 on the sample gas line, a first gas supply line 14 that is used to supply a first gas which contains oxygen to the non-methane cutter 13, and a second gas supply line 15 that is used to supply a second gas which contains hydrogen to the non-methane cutter 13.

One end of the sample gas line 11 is connected to an exhaust pipe or the like of a vehicle, while another end thereof is open, for example, to the outside (i.e., is open to the atmosphere). A suction type of sampling pump (not shown in the drawings) that is used to draw sample gas into the sample gas line 11 is provided downstream from the methane analyzer 12 on the sample gas line 11.

The methane analyzer 12 measures hydrocarbons (HC), which are organic compounds, as compounds that are subject to measurement. In this embodiment, the methane analyzer 12 has a flame ionization detector, and is used to measure methane contained in the sample gas.

The non-methane cutter 13 removes hydrocarbons other than methane (non-methane components) from the sample gas flowing through the sample gas line 11 by combustion (i.e., by oxidization), and is a metal catalyst containing, for example, manganese dioxide or copper oxide or the like.

The first gas supply line 14 is a line through which flows a first gas (i.e., an oxygen-containing gas) that contains oxygen which is required for the removal of non-methane components by the non-methane cutter 13, and one end thereof is connected, for example, to a gas cylinder or the like (not shown in the drawings), while another end thereof is connected to the sample gas line 11 on a forward side of, in other words, upstream from the non-methane cutter 13.

The second gas supply line 15 is a line through which flows a second gas (i.e., a hydrogen-containing gas) that contains hydrogen which is required together with oxygen in order to create water, and one end thereof is connected, for example, to a gas cylinder or the like (not shown in the drawings), while another end thereof is connected to the sample gas line 11 on the forward side of, in other words, upstream from the non-methane cutter 13.

In the present embodiment, a gas mixing line 16 where the first gas and the second gas are mixed together and flow through the gas mixing line 16 is formed downstream from the first gas supply line 14 and the second gas supply line 15. A downstream end of this gas mixing line 16 is connected to the sample gas line 11 upstream from the non-methane cutter 13.

A water supply catalyst 17 that creates water by causing the oxygen in the first gas to react efficiently with the hydrogen in the second gas is provided on the gas mixing line 16.

The gas analysis device 1 of the present embodiment is further provided with a total hydrocarbon analysis line 18 that branches off from the sample gas line 11 upstream from a merging point where the sample gas line 11 merges with the gas mixing line 16.

The total hydrocarbon analysis line 18 is used to analyze total hydrocarbons contained in the sample gas, and is provided with a total hydrocarbon analyzer (i.e., a second analyzer) 181, and a first flow rate control device 182 that controls the flow rate of the sample gas in this total hydrocarbon analysis line 18.

The total hydrocarbon analyzer 181 measures hydrocarbons (HC), which are organic compounds, as compounds subject to measurement. In this embodiment, the total hydrocarbon analyzer 181 has a flame ionization detector, and is used to measure the total hydrocarbons contained in the sample gas.

The first flow rate control device 182 utilizes a fluid resistance element such as a capillary tube or the like having a narrower internal diameter than the flow path to the front and rear thereof, however, the first flow rate control device 182 may also be formed using a mass flow controller or an orifice or the like.

Furthermore, the gas analyzer 1 of the present embodiment is also provided with a non-methane cutter confirmation line 19 that guides the sample gas to the methane analyzer 12 without the sample gas passing through the non-methane cutter 13.

The non-methane cutter confirmation line 19 branches off from the sample gas line 11 upstream from the non-methane cutter 13 so as to detour around the non-methane cutter 13, and merges with the sample gas line 11 downstream from the non-methane cutter 13. Note that the branching point is positioned upstream from the merging point where the sample gas line 11 merges with the gas mixing line 16.

In the present embodiment, a first valve V1 is provided on the sample gas line 11 between the branching point where the non-methane cutter confirmation line 19 branches off from the sample gas line 11 and the merging point where the non-methane cutter confirmation line 19 merges again with the sample gas line 11, and a second valve V2 is provided on the non-methane cutter confirmation line 19. By appropriately opening or closing the first valve V1 and the second valve V2, sample gas can be made to flow through either the sample gas line 11 or the non-methane cutter confirmation line 19.

Moreover, the gas analysis device 1 according to the present embodiment is further equipped with a pressure loss mechanism 20 that controls the flow rate of the sample gas flowing through the sample gas line 11, a pressure control mechanism 21 that performs control such that a pressure difference in the sample gas line 11 between the front and the rear of the pressure loss mechanism 20 remains constant, a first gas pressure adjustment mechanism 22 that performs control such that a difference between the pressure in the sample gas line 11 on the rearward side of the pressure loss mechanism 20 and the pressure in the first gas supply line 14 remains constant, and a second gas pressure adjustment mechanism 23 that performs control such that a difference between the pressure in the sample gas line 11 on the rearward side of the pressure loss mechanism 20 and the pressure in the second gas supply line 15 remains constant.

The pressure loss mechanism 20 is provided in front of the merging point where the sample gas line 11 merges with the gas mixing line 16 and, in this embodiment, for example, a capillary tube (a first capillary tube 20) is used for the pressure loss mechanism 20.

The pressure control mechanism 21 maintains a constant pressure difference in the sample gas line 11 between the front and the rear of the pressure loss mechanism 20 by controlling the pressure on the rearward side of the pressure loss mechanism 20. Specifically, the pressure control mechanism 21 is equipped with a sample pressure adjustment line 211 that is open, for example, to the atmosphere and communicates with the outside, a sample gas discharge line 212 that connects the sample pressure adjustment line 211 to the sample gas line 11 and guides a portion of the sample gas to the sample pressure adjustment line 211, a second capillary tube 213 that serves as a fluid resistance element provided on the sample pressure adjustment line 211, and a sample pressure control device 214 that is provided on the sample pressure adjustment line 211 and adjusts the pressure in the sample pressure adjustment line 211.

One end of the sample pressure adjustment line 211 is connected, for example, to a gas cylinder or the like (not shown in the drawings), and gas supplied from the gas cylinder or the like flows through the interior of the sample pressure adjustment line 211.

One end of the sample gas discharge line 212 is connected to the sample gas line 11 on the rearward side of the pressure loss mechanism 20, while the other end thereof is connected to the sample pressure adjustment line 211. An upstream end of the sample gas discharge line 212 of the present embodiment splits into two branches and one branch is connected to the sample gas line 11, while the other branch is connected to the non-methane cutter confirmation line 19.

In the present embodiment, a fifth capillary tube 24 that controls the flow rate of gas flowing to the non-methane cutter 13 is provided on the rearward side of the connection point between the sample gas line 11 and the sample gas discharge line 212, and on the forward side of the non-methane cutter 13.

In addition, a sixth capillary tube 25 that controls the flow rate of gas flowing to the non-methane cutter confirmation line 19 is provided on the forward side of a second valve V2 of the non-methane cutter confirmation line 19.

The flow rates of the sample gas passing through the fifth capillary tube 24 and the sixth capillary tube 25 are set so as to be lower than the sum total of the flow rate of the sample gas passing through the first capillary tube 20 and the flow rates of the first gas and second gas flowing from the gas mixing line 16 into the sample gas line 11.

By doing this, it is possible to prevent any backflow of sample gas from the sample gas discharge tube 212 back into the sample gas line 11.

Note that whether or not the fifth capillary tube 24 and the sixth capillary tube 25 are to be provided can be appropriately decided based on the circumstances.

The second capillary tube 213 is provided on the sample pressure adjustment line 211 on the rearward side of the connection point thereof with the sample gas discharge line 212.

The sample pressure control device 214 controls the flow rate of the sample gas flowing from the sample gas line 11 or the non-methane cutter confirmation line 19 into the sample gas discharge line 212. Specifically, this sample pressure control device 214 is formed by a sample pressure adjustment valve 214V that is provided on the sample pressure adjustment line 211 upstream from a connection point between the sample pressure adjustment line 211 and the sample gas discharge line 212. The valve opening angle of this sample pressure adjustment valve 214V is controlled by referring to the pressure in the sample gas line 11 on the forward side of the pressure loss mechanism 20.

More specifically, the sample pressure adjustment valve 214V is formed such that it directly senses the pressure in the sample gas line 11 on the forward side of the pressure loss mechanism 20, and changes its valve opening angle accordingly. By employing this structure, the sample pressure adjustment valve 214V controls the pressure in the sample pressure adjustment line 211 by regulating the flow rate of gas flowing through the sample pressure adjustment line 211.

The first gas pressure adjustment mechanism 22 is equipped with a third capillary tube 221 that serves as a fluid resistance element provided on the first gas supply line 14, and a first gas pressure adjustment valve 222 that is provided upstream from the third capillary tube 221.

The third capillary tube 221 controls the flow rate of the first gas flowing through the first gas supply line 14, and causes a pressure loss to be generated in the first gas supply line 14.

The first gas pressure adjustment valve 222 preforms control such that a pressure difference in the first gas supply line 14 between the front and the rear of the third capillary tube 221 remains constant, and the valve opening angle thereof is controlled based, for example, on the pressure in the gas mixing line 16 on the rearward side of the water supply catalyst 17. Here, in the same way as the above-described sample pressure adjustment valve 214V, the first gas pressure adjustment valve 222 is formed such that it directly senses the pressure in the gas mixing line 16 on the rearward side of the water supply catalyst 17, and changes its valve opening angle accordingly. By employing this structure, the first gas pressure adjustment valve 222 controls the pressure in the first gas supply line 14 by adjusting the flow rate of the first gas that is flowing through the first gas supply line 14.

The second gas pressure adjustment mechanism 23 is equipped with a fourth capillary tube 231 that serves as a fluid resistance element provided on the second gas supply line 15, and a second gas pressure adjustment valve 232 that is provided upstream from the fourth capillary tube 231.

The fourth capillary tube 231 controls the flow rate of the second gas flowing through the second gas supply line 15, and causes a pressure loss to be generated in the second gas supply line 15.

The second gas pressure adjustment valve 232 performs control such that a pressure difference in the second gas supply line 15 between the front and the rear of the fourth capillary tube 231 remains constant, and the valve opening angle thereof is controlled based, for example, on the pressure in the gas mixing line 16 on the rearward side of the water supply catalyst 17. Here, in the same way as the above-described sample pressure adjustment valve 214V, the second gas pressure adjustment valve 232 is formed such that it directly senses the pressure in the gas mixing line 16 on the rearward side of the water supply catalyst 17, and changes its valve opening angle accordingly. By employing this structure, the second gas pressure adjustment valve 232 controls the pressure in the second gas supply line 15 by adjusting the flow rate of the second gas that is flowing through the second gas supply line 15.

Next, an operation of the gas analysis device 1 according to the present embodiment will be described.

Firstly, when a sampling pump (not shown in the drawings) is operated, exhaust gas, which is serving as a sample gas, emitted from an internal combustion engine of a vehicle is drawn into the sample gas line 11 and the total hydrocarbon analysis line 18. At this time, if necessary, the sample gas can also be made to pass through a filter F and a capillary tube or the like that controls the flow rate thereof.

The flow rate of the sample gas being sampled is controlled by the first capillary tube 20 and the first flow rate control device 182. Any surplus sample gas that exceeds a predetermined flow rate is discharged to the outside without entering the sample gas line 11 or the total hydrocarbon analysis line 18.

At this time, the sample pressure adjustment valve 214V directly monitors the pressure in the sample gas line 11 on the forward side of the pressure loss mechanism 20.

For example, if the pressure in the sample gas line 11 on the forward side of the pressure loss mechanism 20 rises, the valve opening angle of the sample pressure adjustment valve 214V is increased. This generates an increase in the flow rate in the sample pressure adjustment line 211, and a rise in the pressure between the sample pressure adjustment valve 214V and the second capillary tube 213.

As a result, the pressure difference between the pressure in the sample gas discharge line 212 that is connected to the sample pressure adjustment line 211 and the pressure in the sample gas line 11 is reduced, and the quantity of gas flowing from the sample gas line 11 or the non-methane cutter confirmation line 19 to the sample gas discharge line 212 decreases. Because of this, the pressure in the sample gas line 11 on the rearward side of the pressure loss mechanism 20 rises.

In contrast, if the pressure in the sample gas line 11 on the forward side of the pressure loss mechanism 20 falls, the valve opening angle of the sample pressure adjustment valve 214V is decreased. This generates a decrease in the flow rate in the sample pressure adjustment line 211, and a fall in the pressure between the sample pressure adjustment valve 214V and the second capillary tube 213.

As a result, the pressure difference between the pressure in the sample gas discharge line 212 that is connected to the sample pressure adjustment line 211 and the pressure in the sample gas line 11 is enlarged, and the quantity of gas flowing from the sample gas line 11 or the non-methane cutter confirmation line 19 to the sample gas discharge line 212 increases. Because of this, the pressure in the sample gas line 11 on the rearward side of the pressure loss mechanism 20 falls.

In this way, the sample pressure adjustment valve 214V always maintains a constant pressure difference in the sample gas line 11 on the forward side and on the rearward side of the pressure loss mechanism 20, and the flow rate of the sample gas passing through the first capillary tube 20 is kept constant, thereby helping maintain a constant flow rate of the sample gas in the sample gas line 11 and in the non-methane cutter confirmation line 19.

The sample gas that has passed through the first capillary tube 20 merges via the gas mixing line 16 with the first gas and second gas supplied to the sample gas line 11.

At this time, the first gas pressure adjustment valve 222 and the second gas pressure adjustment valve 232 directly monitor the pressure in the sample gas line 11 on the rearward side of the pressure loss mechanism 20, which, here, is also the pressure in the gas mixing line 16 on the rearward side of the water supply catalyst 17.

For example, if the pressure in the gas mixing line 16 on the rearward side of the water supply catalyst 17 rises, the valve opening angles of both the first gas pressure adjustment valve 222 and the second gas pressure adjustment valve 232 are increased so that the flow rate of the gas flowing through these pressure adjustment valves is increased.

As a result, there is a rise in both the pressure in the first gas supply line 14 between the first gas pressure adjustment valve 222 and the third capillary tube 221, and the pressure in the second gas supply line 15 between the second gas pressure adjustment valve 232 and the fourth capillary tube 231.

On the other hand, if the pressure in the gas mixing line 16 on the rearward side of the water supply catalyst 17 falls, the valve opening angles of both the first gas pressure adjustment valve 222 and the second gas pressure adjustment valve 232 are decreased so that the flow rate of the gas flowing through these pressure adjustment valves 222 and 232 is reduced.

As a result, there is a fall in both the pressure in the first gas supply line 14 between the first gas pressure adjustment valve 222 and the third capillary tube 221, and the pressure in the second gas supply line 15 between the second gas pressure adjustment valve 232 and the fourth capillary tube 231.

In this way, the first gas pressure adjustment valve 222 maintains a constant pressure difference in the sample gas line 11 on the rearward side of the pressure loss mechanism 20 and in the first gas supply line 14 on the forward side of the third capillary tube 221, thereby the flow rate of the first gas supplied to the sample gas line 11 is kept constant.

In addition, the second gas pressure adjustment valve 232 maintains a constant pressure difference in the sample gas line 11 on the rearward side of the pressure loss mechanism 20 and in the second gas supply line 15 on the forward side of the fourth capillary tube 231, thereby the flow rate of the second gas supplied to the sample gas line 11 is kept constant.

At this time, it is preferable that a greater quantity of oxygen than that required to react with the hydrogen in the water supply catalyst 17 so as to form water be contained in the first gas. Namely, it is preferable that the gas supplied from the gas mixing line 16 to the sample gas line 11 be a gas that contains water and oxygen.

By doing this, the sample gas is diluted by merging with the gas containing water and oxygen that is supplied to the sample gas line 11 via the gas mixing line, and then passes through the non-methane cutter 13. The flow rate of this sample gas is appropriately controlled if this is necessary, and the sample gas is then guided to the methane analyzer 12 where it is analyzed.

According to the gas analysis device 1 that is formed in the above-described manner, even if there are variations in the pressure of the sample gas fed to the sample gas line 11 because, for example, of pulsations in the sampling pump, or because of changes in the engine running state due to a driver accelerating or braking, it is still possible to maintain a constant pressure difference between the front and the rear of the pressure loss mechanism 20, and the quantity of sample gas passing through the pressure loss mechanism 20 can be kept constant.

Even if there are variations in the state of a vehicle engine because, for example, of a driver operating the accelerator or the brake so that the pressure on the entry side of the sample gas line 11 varies rapidly, because the pressure in the sample gas line 11 is adjusted on the rearward side of the pressure loss mechanism 20 by referring to the pressure in the sample gas line 11 on the forward side of the pressure loss mechanism 20, the flow rate of the sample gas passing through the pressure loss mechanism 20 can be kept constant.

Moreover, even if there are variations in the pressure in the sample gas line 11, because differences between the pressure in the sample gas line 11 on the rearward side of the pressure loss mechanism 20 and the pressure on the forward side of both the third capillary tube 221 and the fourth capillary tube 231 are respectively kept constant, the flow rates of the first gas and the second gas that are supplied to the sample gas line 11 can be kept constant.

As a result, it is possible to maintain a constant mixture ratio between the sample gas and the first gas and second gas that merge together in the sample gas lime 11 on the rearward side of the pressure loss mechanism 20.

Because of this, the dilution ratios of the sample gas by the first gas and second gas can be kept stable, and the concentration and quantity of methane contained in the sample gas can be accurately measured.

Because the sample gas discharge line 212 is connected to the sample gas line 11 downstream from the merging point where the sample gas line 11 merges with the gas mixing line 16, the gas that is discharged from the sample gas discharge line 212 forms the gas that is created after the sample gas and the first gas and second gas have mixed together, and this makes it difficult for the mixture ratio between the sample gas and the first gas and second gas to change.

It should be noted that, in order for methane components contained in the sample gas to be accurately analyzed by the gas analysis device 1, it is necessary for the non-methane cutter 13 to separate out the methane by combusting all hydrocarbons in the sample gas other than methane.

When these hydrocarbons excluding methane are being combusted by the non-methane cutter 13, there is a concern that, if there is insufficient oxygen, the hydrocarbons excluding methane will not be combusted. There is also a concern that, if too much oxygen is supplied, then the methane will also end up being combusted.

For this reason, consideration may be given to supplying water to the non-methane cutter 13 so as to inhibit methane combustion.

Regarding this point, in the present embodiment, because the quantity of oxygen-containing gas, which is the first gas, supplied to the water supply catalyst 17 is greater than the quantity of hydrogen-containing gas, which is the second gas, oxygen-containing gas, namely, the first gas, and water-containing gas, which contains water generated by the water supply catalyst 17, are supplied to the sample gas line 11.

Because of this, even of the pressure of the sample gas does vary, because it is possible to supply appropriate quantities of oxygen and water consistently to the non-methane cutter 13, the separation capabilities of the non-methane cutter 13 can be adjusted to within a suitable range.

Next, a second embodiment of the gas analysis device 1 according to the present invention will be described with reference made to the drawings.

Figure 2:
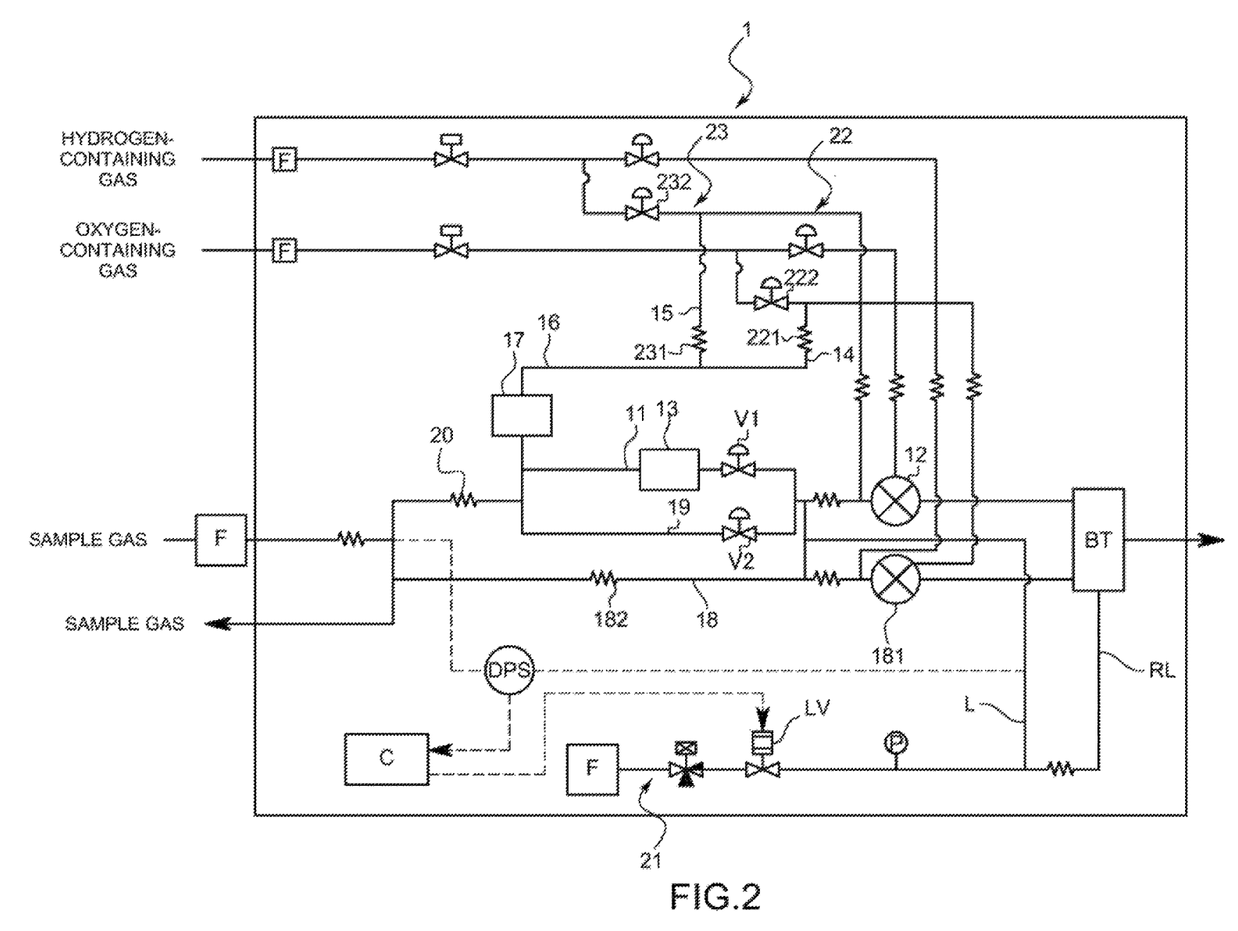
FIG. 2 is a typical view showing the structure of a gas analysis device according to a second embodiment of the present invention.

In the first embodiment a structure is employed in which the pressure control mechanism 21 discharges a portion of the sample gas from the rearward side of the pressure loss mechanism 20, however, as is shown in FIG. 2, in the second embodiment a structure is employed in which the pressure control mechanism 21 supplies a predetermined gas to the rearward side of the pressure loss mechanism 20. Hereinafter, the structure of the pressure control mechanism 21 of the second embodiment will be described in detail.

The pressure control mechanism 21 maintains a constant pressure difference between the front and the rear of the pressure loss mechanism 20 by controlling the pressure on the rearward side of the pressure loss mechanism 20. Specifically, as is shown in FIG. 2, the pressure control mechanism 21 is equipped with a third gas supply line L that supplies a predetermined third gas from the outside to the rearward side of the pressure loss mechanism 20, a pressure control valve LV that is provided on the third gas supply line L, and a control device C that controls the valve opening angle of the pressure control valve LV.

The third gas supply line L supplies atmospheric air that has been drawn in via, for example, a filter F to the downstream side of the pressure loss mechanism 20 as the third gas. Note that it is only necessary that a gas that does not inhibit the analysis of the sample gas by the methane analyzer 12 or the total hydrocarbon analyzer 18 be used as the third gas, and it is also possible, for example, for the sample gas itself, or the first gas or second gas of the first embodiment, or some other gas to be used as the third gas.

This third gas supply line L is connected to a discharge line RL on which a sampling pump (not shown in the drawings) is provided. Note that a buffer tank BT is provided on the discharge line RL.

The pressure control valve LV is provided on the third gas supply line L and controls the flow rate of the third gas. Specifically, the pressure control valve LV is an electromagnetic valve such as a linear valve.

The control device C is a computer that is provided with a CPU, memory, and an A/D converter and the like, and is formed such that it controls the valve opening angle of the pressure control valve LV as a result of the CPU and peripheral devices operating together in accordance with a program stored in a predetermined area of the memory.

Here, a differential pressure gauge DPS is provided to detect pressure differences between the front and the rear of the pressure loss mechanism 20. Pressure differences detected by this differential pressure gauge DPS are transmitted sequentially as differential pressure signals to the control device C. Specifically, this differential pressure gauge DPS detects the pressure difference between the pressure on the upstream side of the pressure loss mechanism 20 and the pressure in the portions between the downstream side of the pressure loss mechanism 20 and the upstream side of the respective analyzers 12 and 181.

Based of the pressure differences shown by the differential pressure signals, the control device C controls the linear valve that is serving as the aforementioned pressure control valve LV. Specifically, the control device C performs feedback control on the valve opening angle of the pressure control valve LV such that the pressure differences shown by the differential pressure signals match previously set target values.

According to the gas analysis device 1 that is formed in the above-described manner, even if there are pressure variations in the sample gas fed to the sample gas line 11 because of pulsations in the sampling pump, or because of changes in the engine running state due to a driver accelerating or braking, the pressure control mechanism 21 is still able to maintain a constant pressure difference between the front and the rear of the pressure loss mechanism 20 (in other words, the pressure difference between the upstream side of the pressure loss mechanism 20 and the merging point where the sample gas line 11 and the third gas supply line L merge together). As a consequence, the flow rate of sample gas passing through the pressure loss mechanism 20 can be kept constant, and the flow rate of sample gas flowing to the methane analyzer 12 and the total hydrocarbon analyzer 181 can be kept constant.

Furthermore, because the pressure control mechanism 21 supplies atmospheric air as the third gas to the rearward side of the pressure loss mechanism 20 such that a constant pressure difference is maintained between the front and the rear of the pressure loss mechanism 20, the sample gas can be kept at a desired dilution ratio, and an improvement in the accuracy of the measurements performed by the methane analyzer 12 and the total hydrocarbon analyzer 181 can be improved.

Note that in the above-described embodiment the pressure control valve LV is digitally controlled by the control device C, however, it is also possible for the control device C to perform analog control on the pressure control valve LV based on detection values obtained from the differential pressure sensor DPS.

Figure 3:
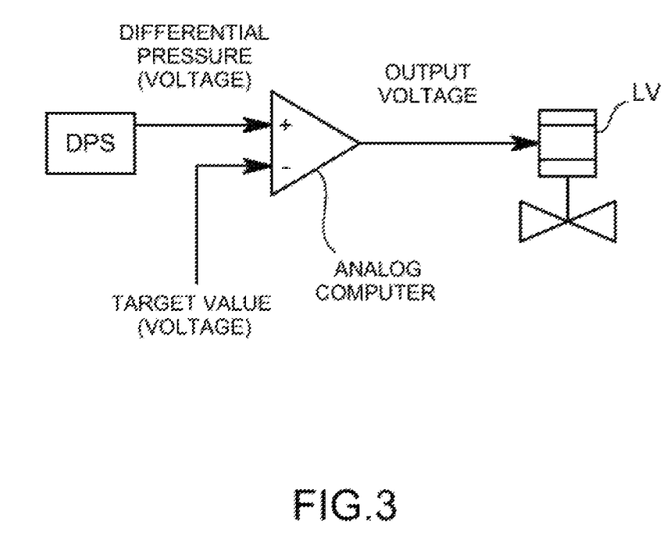
FIG. 3 is a view illustrating a variant example of the gas analysis device according to the second embodiment of the present invention.

Specifically, as is shown in FIG. 3, a structure may be employed in which a voltage showing a detection value obtained from the differential pressure sensor DPS and a voltage showing a target value that has been set in advance are input into an analog computer, and the valve opening angle of the pressure control valve LV is controlled by outputting an output voltage that is based on the difference between these voltages to the pressure control valve LV.

Note that one more point of difference between the above described first embodiment and second embodiment is the fact that the differential pressure gauge DPS is provided in the second embodiment, and the linear valve LV is controlled based on pressure differences detected by the differential pressure gauge DPS. This point is described below more fully.

Figure 4:
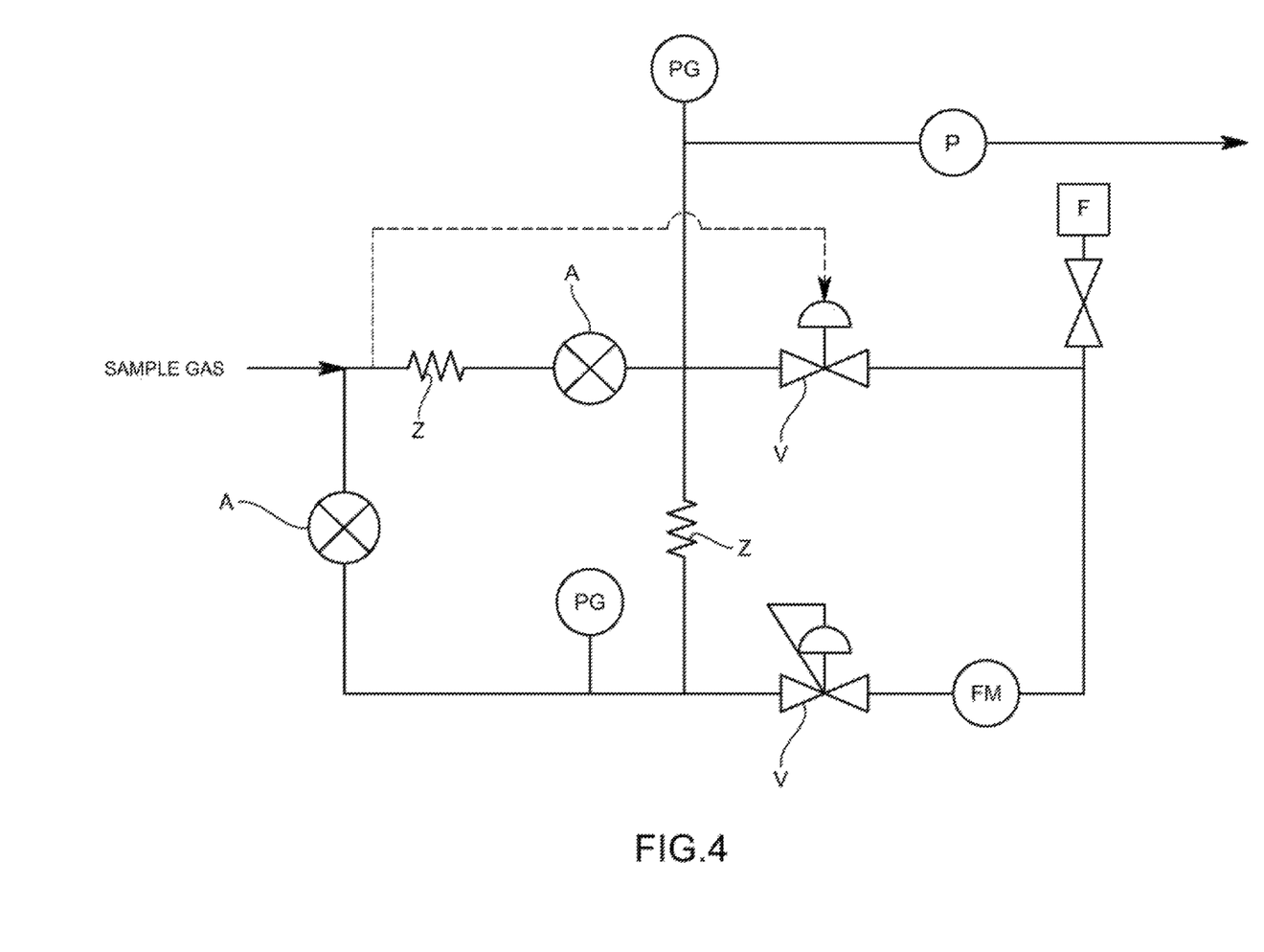
FIG. 4 is a typical view illustrating a gas analysis device according to another embodiment of the present invention.

Firstly, as is shown in FIG. 4, in a structure in which exhaust gas that has been sampled by a sampling pump P is analyzed by an analyzer A such as a methane analyzer or a total hydrocarbon analyzer or the like, a case in which the pressure adjustment valve V is, for example, a diaphragm-type of mechanical pressure adjustment valve will be considered.

In the above-described structure, in order for the flow rate of the exhaust gas flowing into the analyzer A to be kept to a constant flow rate, it is sufficient if the pressure adjustment valve V is controlled such that the pressure difference between the front and the rear of a pressure loss mechanism Z such as a capillary tube or the like is kept constant.

However, if the pressure adjustment valve V is a mechanical type of pressure adjustment valve, then delays in the responsiveness thereof that are caused by variations (i.e. pulsations) in the flow rate of the sampling pump P or by changes in air pressure or the like, as well as hardening of the diaphragm because of changes in the ambient temperature and the like occur. Because of this, in a structure that employs a mechanical type of pressure adjustment valve, it is not possible to maintain a constant pressure difference between the front and the rear of the pressure loss mechanism Z at a desired level of accuracy because of a variety of physical factors and changes in the surrounding environment and the like. As a result, the effects of this appear in the indicated values of the analyzer A, and the problem arises that it is not possible to secure an accurate analysis.

Figure 5:
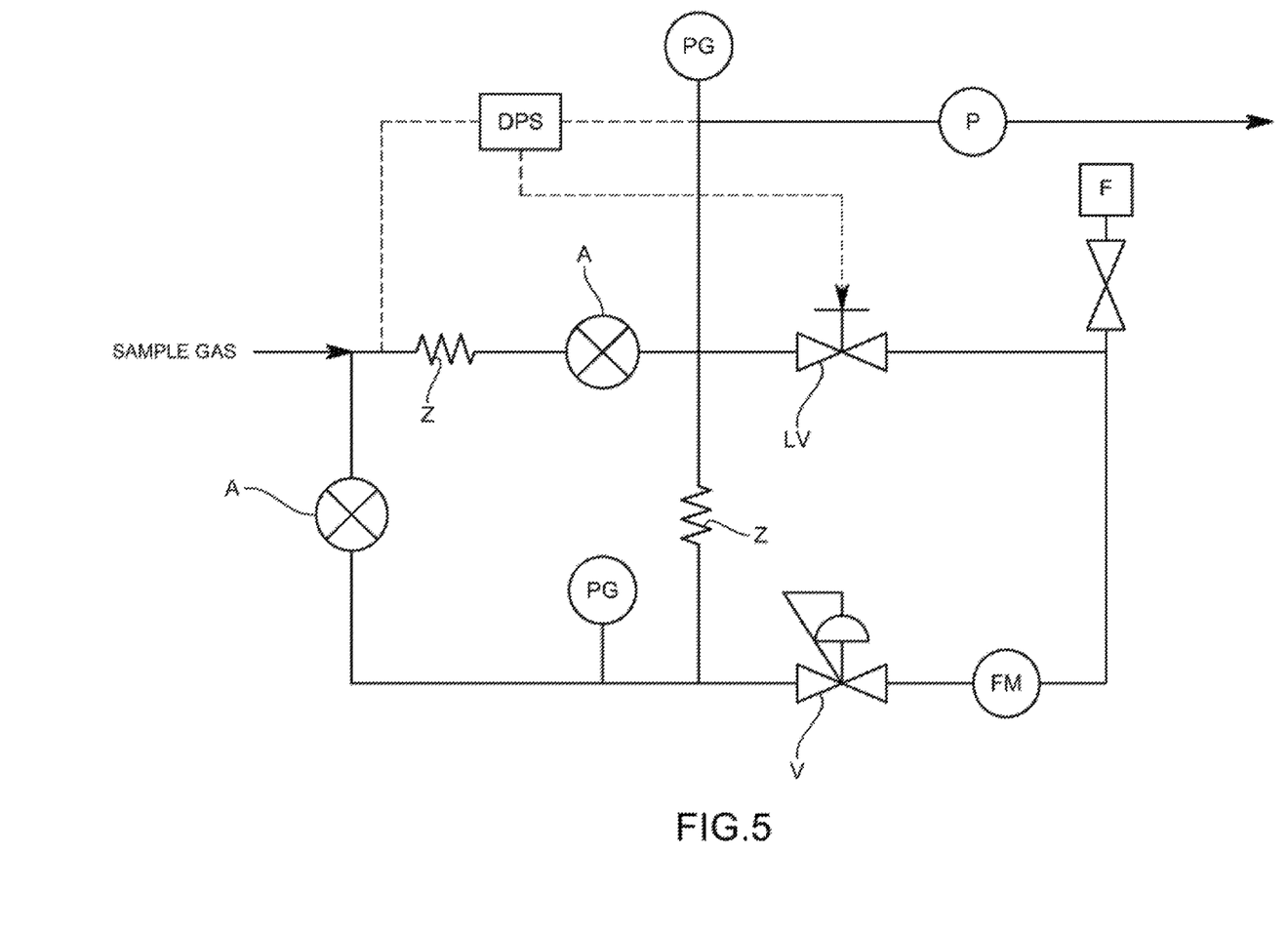
FIG. 5 is a typical view showing the structure of a gas analysis device according to another embodiment of the present invention.

For this reason, in order to solve the above-described problem, the inventors of the present application conceived the structure shown in FIG. 5. Namely, this structure is provided with a linear valve LV on a gas supply line L that supplies a predetermined gas (atmospheric air in this case) to the rearward side of the pressure loss mechanism 20, and with the differential pressure gauge DPS that detects pressure differences between the front and the rear of the pressure loss mechanism Z, and the valve opening angle of the linear valve LV is controlled such that the detection values obtained by the differential pressure gauge DPS are constant.

If the above-described structure is employed, then because the linear valve V is controlled based on detection values obtained by the differential pressure valve DPS, it is possible to reduce to a minimum the effects from the surrounding environment such as the peripheral temperature and air pressure and the like, and it is possible to maintain a constant pressure difference between the front and the rear of the pressure loss mechanism Z at a desired level of accuracy.

Furthermore, because the linear valve LV is controlled based on detection values for the differential pressure detected by the differential pressure valve DPS, the responsiveness is speeded up compared to the structure shown in FIG. 4, and even if variations (i.e., pulsations) in the flow rate of the pump P do occur, the effects from those flow rate variations on the indicated values of the analyzer A are extremely small and the accuracy of the analysis performed by the analyzer A can be secured.

The above-described operation and effects can also be achieved by the gas analysis device 1 of the second embodiment.

Namely, in the second embodiment, because the pressure control mechanism 21 controls pressure differences between the front and the rear of the pressure loss mechanism 20 based on detection values obtained by the differential pressure gauge DPS, it is possible to reduce to a minimum the effects from the surrounding environment such as the peripheral temperature and air pressure and the like, so that even if variations (i.e., pulsations) in the flow rate of the sampling pump do occur, the effects from those flow rate variations on the indicated values of the respective analyzers 12 and 181 can also be reduced to a minimum.

In addition to this, if it is possible to sufficiently reduce the effects from variations in the flow rate of the sampling pump, then it also becomes possible to eliminate the need for the buffer tank BT, and a reduction in the size of the device can be achieved.

Note that the present invention is not limited to the above-described respective embodiments.

For example, a gas sampling device that samples a sample gas, and is provided with the sample gas line 11 described in each of the foregoing embodiments, the pressure loss mechanism 20, and the pressure control mechanism 21 is also one aspect of the present invention.

The pressure control mechanism 21 may also be one that supplies a predetermined gas to the sample gas line 11 on the rearward side of the pressure loss mechanism 20.

The predetermined gas may be any gas that does not impede the analysis of the sample gas by the methane analyzer 12, and may be either the sample gas itself, or may be the first gas, the second gas, or a gas other than these.

The sample pressure adjustment valve 214V is not restricted to being a valve type that directly senses the pressure in the sample gas line 11 on the forward side of the pressure loss mechanism 20. For example, it is also possible for the pressure that has been measured by a pressure sensor or the like that is disposed on the sample gas line 11 on the forward side of the pressure loss mechanism 20 to be output to an information processing device (not shown in the drawings), and for this information processing device to then output a command signal to the sample pressure adjustment valve 214V so as to regulate the valve opening angle thereof. This information processing device may be equipped with a CPU, memory, communication ports, and an A/D converter and the like, and may be either specially designed for dedicated use in the gas analysis device 1, or may be a general use computer or the like.

In the same way, the first gas pressure adjustment valve 222 and the second gas pressure adjustment valve 232 are not restricted to being valve types that directly sense the pressure in the gas mixing line 16. For example, it is also possible for the pressure that has been measured by a pressure sensor or the like that is disposed on the gas mixing line 16 to be output to an information processing device, and for this information processing device to then output command signals to each of the first gas pressure adjustment valve 222 and the second gas pressure adjustment valve 232 so as to regulate the valve opening angles thereof.

The water supply catalyst 17 is used to improve the reaction efficiency between oxygen and hydrogen in the gas mixing line 16. Because oxygen and hydrogen that have been mixed together inside the gas mixing line 16 are able to react naturally so as to create water even if the water supply catalyst 17 has not been provided, the water supply catalyst 17 is not an indispensible part of the structure of the gas analysis device 1. Because of this, it is not essential that the gas analysis device 1 be provided with the water supply catalyst 17.

It is also possible for the first gas supply line 14 and the second gas supply line 15 to not merge together, but to instead be connected independently of each other to the sample gas line 11.

Figure 6:
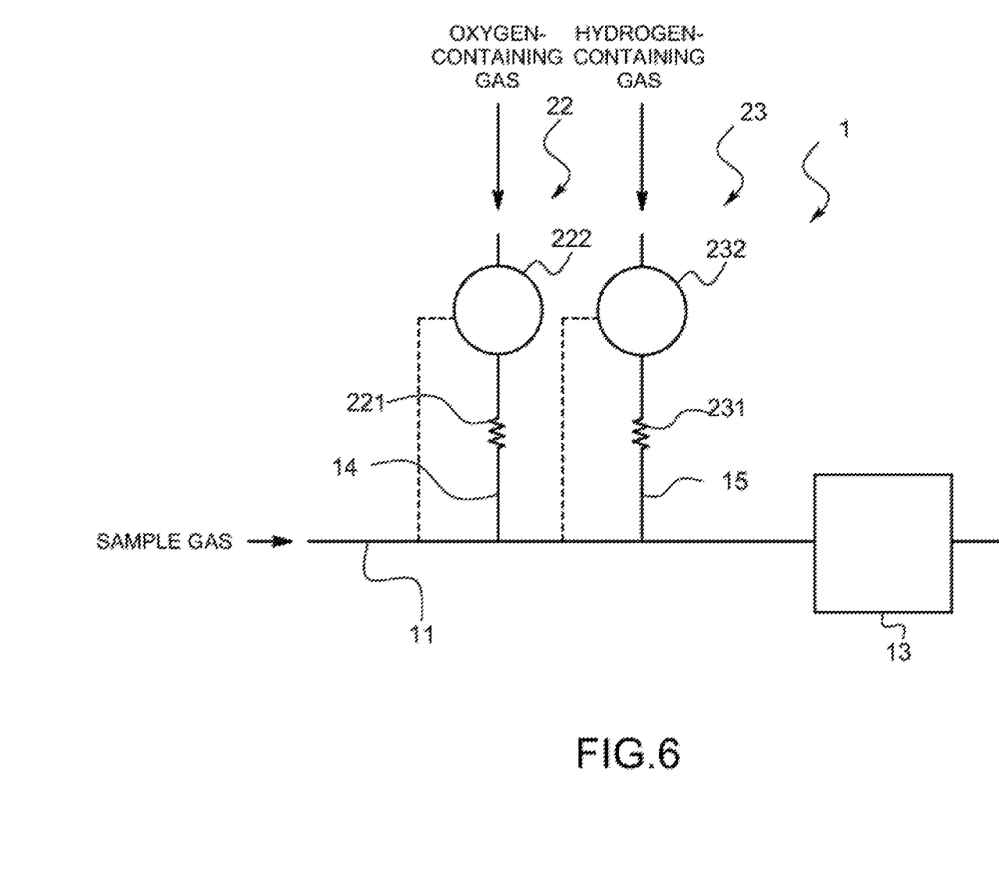
FIG. 6 is a typical view showing the structure of a gas analysis device according to another embodiment of the present invention.

For example, as is shown in FIG. 6, it is also possible for the gas analysis device 1 to be supplied with either water or a water-containing gas as the second gas directly from an external source.

Furthermore, it is also possible for a water-containing gas supplied directly from an external source to be used for the first gas, and for this first gas to contain a predetermined quantity of oxygen.

The oxygen-containing gas may be a gas that contains only oxygen, or may be a gas mixture such as, for example, atmospheric air that contains oxygen in a predetermined concentration.

In the same way, the hydrogen-containing gas may be a gas that contains only hydrogen, or may be a gas mixture that contains hydrogen in a predetermined concentration.

The first gas and second gas are not limited to gases that contain oxygen, hydrogen, or water and, depending on the aim of the analysis, nitrogen-containing gas, helium-containing gas, or various other gases may also be used.

The position where the sampling pump is disposed is not limited to the rearward side of the methane analyzer 12, and it may also be disposed on the forward side of the pressure loss mechanism 20.

The gas analysis device 1 according to the present invention is not limited to being mounted in a vehicle or the like and analyzing exhaust gas from that vehicle, and may also be installed in a test chamber or the like and used to analyze exhaust gas from a vehicle or the like. Furthermore, the gas analysis device 1 is not limited to analyzing exhaust gas from a vehicle and the like, and may also be used to analyze components in a wide variety of sample gases such as environmental gas and the like.

Moreover, the component that is subject to analysis is not limited to methane, and components containing other components such as, for example, total hydrocarbons, nitrogen, oxygen, hydrogen, carbon, and sulfur may also be subjected to analysis.

The analyzer that is used is not limited to the aforementioned flame ionization detector, and it is also possible to use any one of a variety of analyzers that employ methods such as non-dispersive infrared absorption, chemiluminescence detection, magnetic pressure, zirconia analysis, FTIR, mid-infrared laser spectroscopy, gas chromatography, or liquid chromatography to analyze components in a sample gas, or to use various combinations of these analyzers.

The only requirement for the pressure loss mechanism 20 is that it be able to generate pressure loss in the sample gas line 11, and while capillary tubes are employed in the above-described embodiments, it is also possible for orifices or back pressure valves or the like to be employed.

Each of the second through sixth capillary tubes, as well as the first flow rate control device 182 are not limited to being capillary tubes, and it is also possible to utilize orifices or back pressure valves or the like for these as well.

Furthermore, it should be understood that the present invention is not limited to the above-described embodiment, and that various modifications and the like may be made thereto insofar as they do not depart from the spirit or scope of the present invention.

DESCRIPTION OF THE REFERENCE NUMERALS

1 . . . Gas analysis device
11 . . . Sample gas line
12 . . . Methane analyzer
13 . . . Non-methane cutter
14 . . . First gas supply line
15 . . . Second gas supply line
17 . . . Water supply catalyst
20 . . . Pressure loss mechanism
21 . . . Pressure control mechanism
211 . . . Sample pressure adjustment line
212 . . . Sample gas discharge line
214 . . . Sample pressure control device
22 . . . First gas pressure adjustment mechanism
23 . . . Second gas pressure adjustment mechanism

What is claimed is:

1. A gas analysis device comprising:
   a sample gas line through which a sample gas flows;
   a pressure loss mechanism that is provided on the sample gas line;
   a pressure control mechanism that controls pressure differences in the sample gas line between a front and a rear of the pressure loss mechanism by performing an operation from the group consisting of discharging a portion of the sample gas from a rearward side of the pressure loss mechanism, or supplying a predetermined gas to the rearward side of the pressure loss mechanism; and
   an analyzer that analyzes the sample gas flowing through the sample gas line.

2. The gas analysis device according to claim 1, wherein the pressure control mechanism is provided with:
   a sample gas discharge line that discharges a portion of the sample gas in the sample gas line from a rearward side of the pressure loss mechanism;
   a sample pressure adjustment line that is connected to the sample gas discharge line; and
   a sample pressure control device that controls pressure differences between the pressure in the sample gas line on the forward side of the pressure loss mechanism and the pressure in the sample pressure adjustment line by referring to the pressure in the sample gas line on the forward side of the pressure loss mechanism.

3. The gas analysis device according to claim 1, wherein the pressure control mechanism is provided with:
   a gas supply line that supplies a predetermined gas to the sample gas line on the rearward side of the pressure loss mechanism;
   a pressure control valve that is provided on the gas supply line; and
   a differential pressure gauge that detects pressure differences between the front and the rear of the pressure loss mechanism, wherein
   the pressure control valve is controlled based on the pressure differences detected by the differential pressure gauge.

4. The gas analysis device according to claim 1, wherein the pressure loss mechanism is any one of a capillary tube, an orifice, or a back pressure valve.

5. The gas analysis device according to claim 1, wherein there are further provided:
   a first gas supply line that supplies a first gas to the sample gas line on the rearward side of the pressure loss mechanism; and
   a first gas pressure adjustment mechanism that, by referring to the pressure in the sample gas line on the rearward side of the pressure loss mechanism, maintains a constant pressure difference between a supply side pressure in the first gas supply line and the pressure in the sample gas line.

6. The gas analysis device according to claim 1, wherein a non-methane cutter that removes hydrocarbon components other than methane from the sample gas is further provided between the pressure loss mechanism and the analyzer on the sample gas line.

7. The gas analysis device according to claim 1, wherein there are further provided:
- a second gas supply line that supplies a second gas to the sample gas line on the rearward side of the pressure loss mechanism; and
- a second gas pressure adjustment mechanism that, by referring to the pressure in the sample gas line on the rearward side of the pressure loss mechanism, maintains a constant pressure difference between a supply side pressure in the second gas supply line and the pressure in the sample gas line.

8. The gas analysis device according to claim 7, wherein the first gas is oxygen and the second gas is hydrogen, and a water supply catalyst that causes the first gas and the second gas to react so as to create water is further provided on the forward side of the non-methane cutter.

9. The gas analysis device according to claim 8, wherein the quantity of the first gas that is supplied is greater than the quantity of the first gas that reacts with the second gas.

10. The gas analysis device according to claim 9, wherein the sample gas is diluted by the first gas that remains as a result of the reaction between the first gas and the second gas.

11. The gas analysis device according to claim 10, wherein the sample gas discharge line discharges a portion of the sample gas that has been diluted by the first gas from the rearward side of the water supply catalyst.

12. The gas analysis device according to claim 1, wherein the gas analysis device is further provided with a suction type of sampling pump that is disposed downstream from the analyzer on the sample gas line.

13. The gas analysis device according to claim 1, wherein the sample gas is exhaust gas emitted from an internal combustion engine.

14. The gas analysis device according to claim 1, wherein the sample gas is exhaust gas emitted from a vehicle, and the gas analysis device is a vehicle-mounted type of gas analysis device.

15. A gas sampling device comprising:
- a sample gas line through which a sample gas flows;
- a pressure loss mechanism that is provided on the sample gas line; and
- a pressure control mechanism that controls pressure differences in the sample gas line between a front and a rear of the pressure loss mechanism by performing an operation from the group consisting of discharging a portion of the sample gas from a rearward side of the pressure loss mechanism, or supplying a predetermined gas to the rearward side of the pressure loss mechanism.

16. A gas analysis method that employs a gas analysis device that is provided with:
- a sample gas line through which a sample gas flows;
- a pressure loss mechanism that is provided on the sample gas line; and
- an analyzer that analyzes the sample gas flowing through the sample gas line, wherein
- pressure differences in the sample gas line between a front and a rear of the pressure loss mechanism are controlled by performing an operation from the group consisting of discharging a portion of the sample gas from a rearward side of the pressure loss mechanism, or supplying a predetermined gas to the rearward side of the pressure loss mechanism.

* * * * *